United States Patent [19]

Korthoff et al.

[11] Patent Number: 4,667,674
[45] Date of Patent: May 26, 1987

[54] SURGICAL FASTENER EXHIBITING IMPROVED HEMOSTASIS

[75] Inventors: Herbert W. Korthoff, Wilton; David T. Green, Norwalk, both of Conn.

[73] Assignee: United States Surgical Corporation, Norwalk, Conn.

[21] Appl. No.: 741,707

[22] Filed: Jun. 5, 1985

Related U.S. Application Data

[63] Continuation of Ser. No. 538,930, Oct. 4, 1983, abandoned.

[51] Int. Cl.$^4$ .............................................. A61B 17/04
[52] U.S. Cl. .......................... 128/334 C; 227/DIG. 1
[58] Field of Search ............... 128/334 R, 334 C, 337, 128/335, 325, 326; 227/DIG. 1; 411/469, 450, 457

[56] References Cited

U.S. PATENT DOCUMENTS

| | | |
|---|---|---|
| 2,380,655 | 7/1945 | Lang ........................................ 85/49 |
| 2,384,475 | 9/1945 | Lang . |
| 3,166,072 | 1/1965 | Sullivan, Jr. . |
| 3,258,012 | 6/1966 | Nakayama et al. . |
| 3,357,296 | 12/1967 | Lefever ........................ 128/334 C X |
| 3,595,201 | 7/1971 | Oudenhoven . |
| 3,598,299 | 8/1971 | Johnson . |
| 3,641,804 | 2/1972 | Oudenhoven . |
| 3,744,495 | 7/1973 | Johnson . |
| 3,812,859 | 5/1974 | Murphy et al. ...................... 128/330 |
| 3,879,783 | 4/1975 | Giulie . |
| 3,899,914 | 8/1975 | Akiyama . |
| 3,924,629 | 12/1975 | Akiyama . |
| 3,926,193 | 12/1975 | Hasson . |
| 4,060,089 | 11/1977 | Noiles . |
| 4,278,091 | 7/1981 | Borzone . |
| 4,402,445 | 9/1983 | Green .......................... 128/334 R X |
| 4,434,796 | 3/1984 | Karapetian et al. ................ 128/335 |

FOREIGN PATENT DOCUMENTS 2185353  4/1974  France .
972731  10/1964  United Kingdom .

Primary Examiner—Michael H. Thaler
Attorney, Agent, or Firm—Thomas R. Bremer

[57] ABSTRACT

A surgical fastener comprising a fastener member and a retainer member is disclosed. The fastener provides improved hemostasis and, desirably, is of a resinous material that is absorbable in the body. The fastener member has prongs which extend substantially perpendicularly from a base to interlock with apertures in the retainer member. The base and the retainer member are substantially equal in length, and each prong extends from a point on the base spaced inward from its respective end of the base. The fasteners are preferably applied by apparatus including a pusher associated with each fastener member and having a particular structural relationship to the associated fastener member.

14 Claims, 7 Drawing Figures

SURGICAL FASTENER EXHIBITING IMPROVED HEMOSTASIS

This is a continuation, of application Ser. No. 538,930, filed Oct. 4, 1983, entitled SURGICAL FASTENER EXHIBITING IMPROVED HEMOSTASIS now abandoned.

BACKGROUND OF THE INVENTION

This invention relates to surgical fasteners (e.g., staples), and more particularly to a fastener comprising a fastener member and a retainer member and exhibiting improved hemostasis.

Surgical fastening devices allow a surgeon to fasten body tissue by applying surgical fasteners. The fasteners may be applied singly in succession or a number may be applied simultaneously. Surgical fasteners are often made of metals such as tantalum and stainless steel, which are inert. Fasteners of magnesium, which fasteners are gradually absorbed by the body, are also known.

Non-metallic fasteners are also known and may be preferable to metal fasteners in some procedures. For example, non-metallic fasteners can be made X-ray transparent so that they do not scatter X-rays and therefore do not degrade the quality of radiographs as may happen when metal fasteners are used.

On the other hand, objects of non-metallic resinous materials are usually too resilient (i.e., elastic) to hold deformed shapes (assuming plastic flow does not occur). (As used herein, the term "resinous materials" means non-metallic materials, such as natural or synthetic polymers and resins, including protein-based materials, which are relatively flexible and elastic, and which may or may not be absorbable in the body.) The greater elasticity of resinous materials generally makes it impossible to directly substitute such materials for the metal in conventional surgical fasteners.

To overcome this problem, resinous surgical fasteners may be made of two parts: a fastener member and a retainer member. The legs or prongs of the fastener member are driven through one side of the tissue to be fastened and the retainer member interlocks with the prongs of the fastener member on the other side of the tissue to hold the entire fastener structure in place. One such fastener structure and apparatus for applying it are disclosed in Green U.S. Pat. No. 4,402,445, issued Sept. 6, 1983, which is hereby incorporated by reference in its entirety.

A frequent goal in fastening tissue is achieving hemostasis along the fastener line. Hemostasis is achieved by exerting pressure on the tissue from both sides. If metal staples are used, that pressure (hereinafter referred to as "hemostatic pressure") is exerted by and between the base of the staple on one side of the tissue and the crimped legs on the other side of the tissue. In typical crimped metal staples no part of the staple extends beyond the ends of the base. Therefore, a second staple can be applied very close to the first staple, so that the bases of the two staples are in a line. In that case the gap between staples can be quite small so that hemostatic pressure is applied uniformly along the entire staple line.

In contrast, when two-part resinous fasteners are used, hemostatic pressure is exerted by and between the retainer member and the base of the fastener member. In known two-part resinous fasteners the prongs of the fastener member extend from the ends of the base. The retainer member is typically longer than the distance between the prongs and therefore must extend beyond the fastener member base. Accordingly, the bases of adjacent fastener members lying in a line are separated by at least the sum of the distances by which adjacent retainer members extend beyond the associated fastener member bases. Thus, there are gaps between adjacent fastener members. Full hemostatic pressure is not exerted on the tissue in these gaps.

One way to make up for the above-mentioned gaps in a line of resinous fasteners is to apply the fasteners in two parallel rows, with a linear offset between the rows so that the gaps in one row are opposite the bases of the fastener members of the other row. However, this doubles the number of fasteners that are required and increases the area of tissue affected by the fasteners.

Another typical characteristic of resinous materials is that they are not as strong as metals. Surgical fasteners of resinous materials may therefore tend to deform during application to tissue. In particular, the fastener member prongs may tend to splay or spread apart as the prongs are forced through the tissue. One way to overcome this tendency is to provide a metal guide pin adjacent each prong to help the prong penetrate the tissue without deformation. After the fasteners have been applied, the guide pins are withdrawn from the tissue. This guide pin structure has the disadvantage that it increases the complexity and cost of the apparatus for applying the fasteners.

SUMMARY OF THE INVENTION

In accordance with this invention, a surgical fastener that exerts hemostasic pressure along its entire length and cooperates with the applying apparatus to minimize splaying of the prongs is provided. The surgical fastener comprises a fastener member and a retainer member and is applied to tissue in a row in which the lengths of the fasteners are in a line and in which adjacent fasteners are nearly touching each other.

The fastener member comprises (1) a base and (2) a pair of substantially parallel prongs extending substantially perpendicularly from the base in substantially the same direction, each prong being spaced inward from its respective end of the base. Preferably, the base is the same length as the retainer member. Also preferably, the prongs are substantially equidistant from the transverse centerline of the base.

A fastener-applying apparatus for use with the fastener of this invention contains a number of pusher members corresponding to the number of fasteners to be fired. A plurality of retainer members and a corresponding number of fastener members are positioned within the apparatus. The pusher members force the fastener members through tissue into engagement with the retainer members by pushing the bases of the fastener members. The length of each pusher member parallel to the longitudinal axis of the associated fastener member base is substantially equal to the length of the associated fastener member base, and each pusher member exerts pressure along substantially the entire length of each fastener member base.

The present invention finds its greatest use with surgical fasteners of resinous materials, although the invention may be used with fasteners of other materials that have separate fastener and retainer members. A preferred resinous material, which is absorbable in the body, is disclosed in copending, commonly-assigned Kaplan et al. U.S. patent application Ser. No. 436,056, filed Oct. 22, 1982, now U.S. Pat. No. 4,523,591 hereby incorporated by reference in its entirety.

Thus, the present invention provides a surgical fastener that exerts hemostatic pressure along its entire length and cooperates with fastener-applying apparatus to reduce splaying of the prongs of the fastener while the fastener is being applied to tissue.

BRIEF DESCRIPTION OF THE DRAWINGS

The above and other advantages of the present invention will be more apparent after consideration of the accompanying drawings in which like parts are indicated by like reference characters throughout and in which.

DETAILED DESCRIPTION OF THE INVENTION

Figure 1:
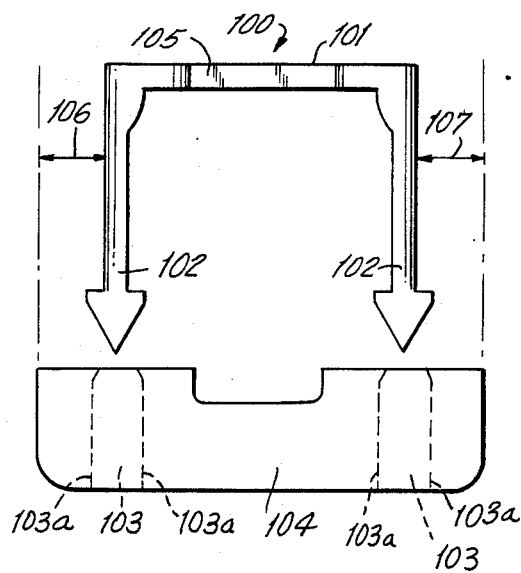
FIG. 1 is an elevational view of a known surgical fastener.

Surgical fastener 100 in FIG. 1 includes retainer member 104 and fastener member 101, which has two prongs 102 depending from base 105. Prongs 102 are driven through tissue to engage apertures 103, whose sidewalls are indicated by dashed lines 103a, in retainer member 104. Both members may be made from a resinous material which may or may not be absorbable in the body.

When fastener 100 is applied to tissue, full hemostatic pressure may not be exerted in the areas represented by arrows 106 and 107. This can be seen more clearly in FIG. 2, which shows two fasteners 100 applied to tissue layers 201 and 202. Full hemostatic pressure is exerted along area 203, but such pressure may not be exerted in area 204, which includes adjacent areas 106 and 107. As a result, there is a gap 205 through which body fluids (e.g., blood, plasma) may seep.

Figure 3:
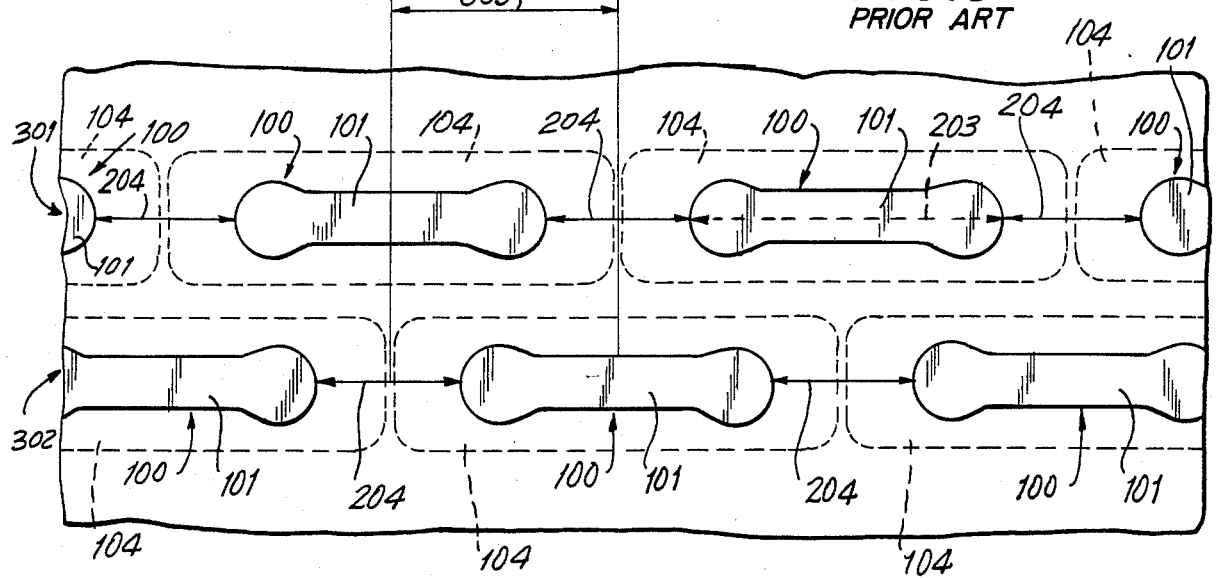
FIG. 3 is a fragmentary plan view of tissue fastened with such fasteners.

Thus, when using fasteners 100, two offset rows 301 and 302 of fasteners are customarily used (see FIG. 3). Because of offset 303 between rows 301 and 302, each area 204 in one row is opposite an area 203 in the other row. Seepage of fluids through any gaps 205 in one row is arrested at corresponding areas 203 in the other row.

Figure 4:
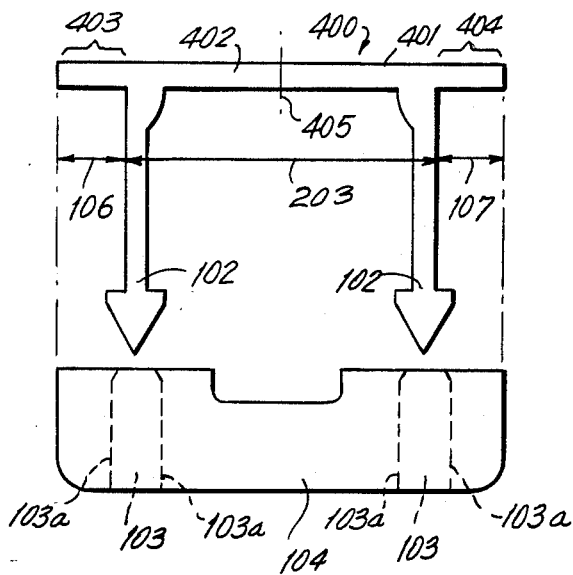
FIG. 4 is an elevational view of a surgical fastener according to the present invention.

The present invention reduces or eliminates the need for a second row of fasteners to provide total hemostasis. Fastener 400 according to the present invention is shown in FIG. 4. Preferred fastener member 401 can be described as "pi-shaped" because of its resemblance to the Greek letter pi. Base 402 of fastener member 401 has extensions 403 and 404, which extend over areas 106 and 107. The retainer member and the base of the fastener member have substantially the same length; the sum of the lengths of extensions 403 and 404 is substantially equal to the sum of the lengths of areas 106 and 07 of FIG. 1. Thus, hemostatic pressure is exerted between extensions 403 and 404 and the corresponding portions of retainer member 104 extending beyond each aperture 103. By applying fasteners 400 close together in a line, total hemostasis can be provided with only a single row of fasteners.

Figure 2:
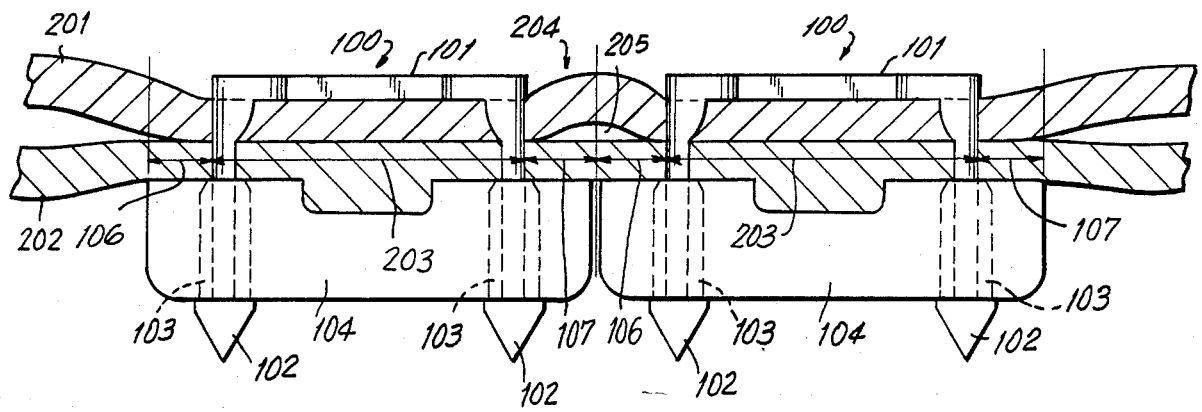
FIG. 2 is a cross-sectional view of tissue fastened with such fasteners.
Figure 5:
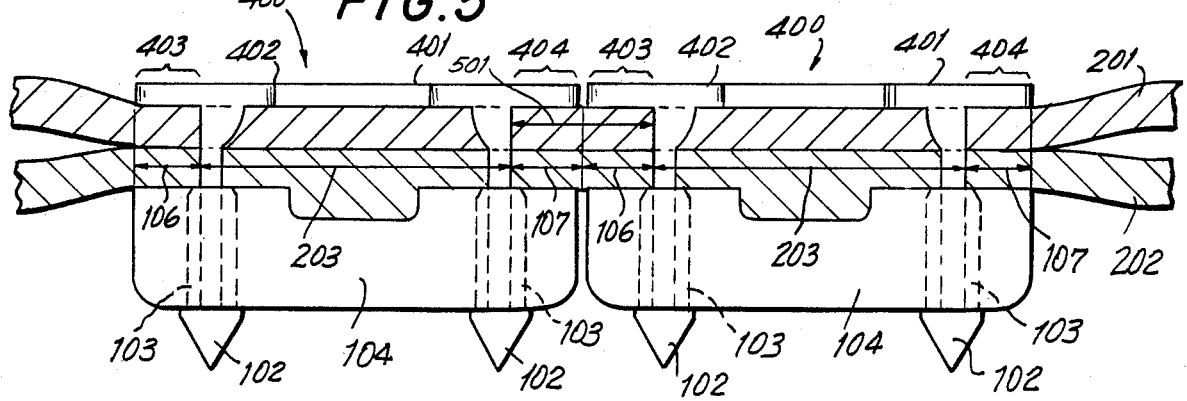
FIG. 5 is a cross-sectional view of tissue fastened with such fasteners.

This is illustrated in FIG. 5. There full hemostatic pressure is exerted in area 501 as well as in areas 203. That is in contrast to the previously known fasteners, as seen in FIG. 2, where full hemostatic pressure may not be exerted in area 204.

Returning to FIG. 4, apertures 103 are usually located symmetrically along the length of retainer member 104 so that areas 106 and 107 are substantially equal in length. Extensions 403 and 404 of base 402 of fastener member 401 are therefore preferably also substantially equal in length, with prongs 102 substantially equidistant from transverse centerline 405 of base 402. However, these conditions are not necessary. It is only necessary that the lengths of the fastener and retainer members be substantially the same. That will provide the desired total hemostasis.

The fasteners shown in FIG. 5 are shown with small gaps between adjacent fasteners. These gaps are shown because it is usually necessary to have some structure in the fastener-applying apparatus (not shown) to separate the channels through which the individual fastener members are guided towards the tissue. During application of the fasteners the tissue is generally compressed by the fastener-applying apparatus, thereby stretching the tissue. When the fastener-applying apparatus is removed from the tissue, the tissue tends to resume its former shape. That brings the fasteners in the tissue closer together so that they are touching or nearly touching. It is desirable that adjacent fasteners in the tissue be nearly touching to provide full hemostasis, although there should preferably be some gap because it is also desirable that the fastener line be somewhat flexible on the tissue. (As used herein, "nearly touching" means touching or separated by a gap of between 0 mm and about 0.5 mm.)

Figure 6:
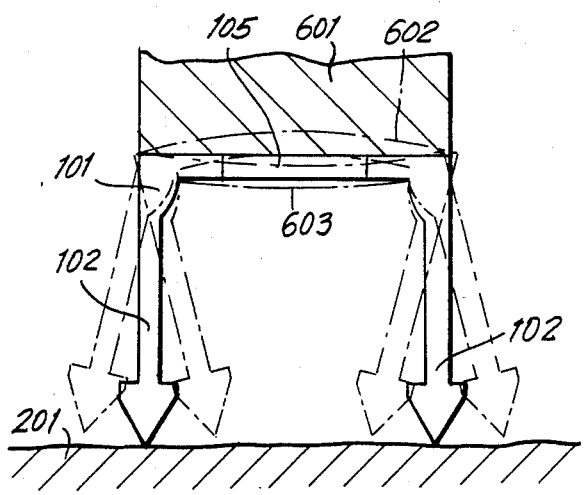
FIGS. 6 and 7 are, respectively, fragmentary cross-sectional views of the fastener members of FIGS. 1 and 4 being applied to tissue by the pusher members of fastener-applying apparatus.
Figure 7:
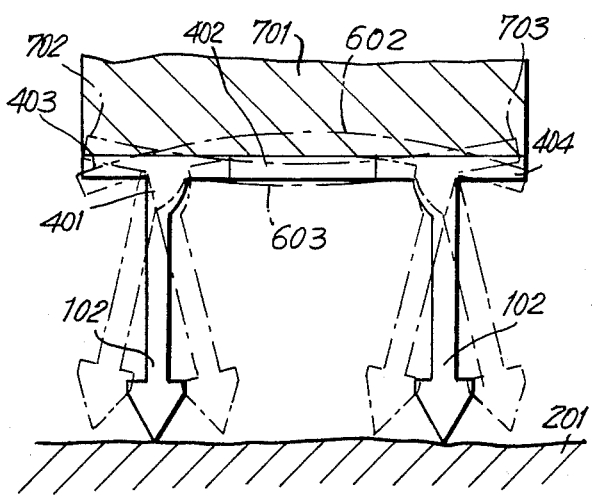

FIGS. 6 and 7 show the beneficial effect of extensions 403 and 404, in combination with fastener-applying pushers 701 (which are longer, parallel to the longitudinal axis of the fastener member base, than would otherwise be employed), in counteracting the tendency of prongs 102 to splay. FIG. 6 shows known fastener member 101 as it is about to pierce tissue 201 under the downward urging of pusher 601 in known fastener-applying apparatus (not otherwise shown). FIG. 7 shows fastener member 401 of this invention in the same position. In accordance with the present invention, pusher 701 is longer, in the direction parallel to the base of the fastener member, than pusher member 601 for fasteners of comparable size. In particular, pusher member 701 is preferably substantially equal in length in the above-identified direction to base 402 of fastener member 401, including extensions 403 and 404. As a consequence, pusher member 701 contacts fastener member 401 along the entire length of base 402. Pusher member 701 should not be measurably longer in that direction than base 402; otherwise, it would prevent adjacent fastener members from being applied to the tissue as close together as possible, which is necessary to provide hemostasis. In other respects the fastener-applying apparatus may be conventional, as exemplified by the above-identified Green patent, although the present invention may facilitate the provision of fastener-applying apparatus as shown in that patent without the metal guide pins.

During the application of resinous fasteners, because both the tissue and fastener member are non-rigid, prongs 102 may tend to bend inward or outward. If prongs 102 try to bend inward, the base of either fastener member 101 or 401 bows upward as indicated at 602 in FIGS. 6 and 7. Such upward bowing is prevented by the presence of pusher 601 or pusher 701 in either device.

If prongs 102 splay or spread apart, the base of either fastener member 101 or 401 bows downward. As shown in FIG. 6, with known fastener member 101 base 105 is not prevented from bowing downward as indicated at 603. In contrast, for fastener member 401 of this invention, if base 402 tries to bow downward, extensions 403 and 404 try to bend upward, as shown in FIG. 7 at 702 and 703. However, upward movement of extensions 403 and 404 is resisted by pusher 701, which is as long as base 402 and exerts pressure along the entire length of base 402. Thus, the combination of longer pusher 701 and extensions 403 and 404 reduces the tendency of prongs 102 of the new fastener to splay.

One skilled in the art will recognize that the inventive principles disclosed herein can be practiced in other than the embodiments described, and the invention is not limited by those embodiments but only by the claims which follow.

We claim:

1. In combination:
   apparatus for applying a plurality of surgical fasteners to body tissue, each of the fasteners having a fastener member and a retainer member;
   a plurality of retainer members positioned within the apparatus, said retainer members being oriented in a row such that the longitudinal centerlines thereof extend substantially in the direction of the row, each retainer member nearly touching each retainer member adjacent thereto; and
   a corrsponding number of fastener members positioned within the apparatus, each of the fastener members comprising a base and a pair of substantially parallel tissue-piercing prongs extending substantially perpendicularly from the base, the length of the base being substantially equal to the length of the retainer member, each prong being spaced inward from its respective end of the base thereby defining tissue-engaging extensions of the base between each prong and its respective end of the base, said fastener members being oriented in a row parallel to said row of retainer members such that the longitudinal centerlines of said fastener members extend substantially in the direction of the row and the tissure-engaging extensions of each fastener member in the row nearly touch a tissure-engaging extension of each fastener member adjacent thereto, thereby providing essentially total hemostasis when the fasteners are applied to tissue.

2. The combination of claim 1 wherein the apparatus further comprises a number of pusher members corresponding to the number of fastener members for pushing the fastener members through tissue into engagement with the retainer members, the length of the face of each pusher member parallel to the base of each fastener member being substantially equal to the length of the base of each fastener member so that when each pusher member contacts the base of its respective fastener member, the pusher member exerts pressure along substantially the entire length of the base of its respective fastener member.

3. The combination of claim 2 wherein the fastener members and retainer members are made of a resinous material.

4. The combination of claim 3 wherein the resinous material is absorbable in the body.

5. The combination of claim 2 wherein the prongs of the fastener member are substantially equidistant from the transverse centerline of the base of the fastener member.

6. The combination of claim 5 wherein the fastener members and retainer members are made of a resinous material.

7. The combination of claim 6 wherein the resinous material is absorbable in the body.

8. In combination:
   a plurality of surgical fasteners for application to body tissue, each of the fasteners having a fastener member and a retainer member, and an apparatus for applying said plurality of fasteners to said body tissue, said apparatus including pusher means for pushing the fastener members through tissue into engagement with the retainer members;
   said retainer members being oriented in a row in each apparatus such that the longitudinal centerlines thereof extend substantially in the direction of the row, each retainer member nearly touching each retainer member adjacent thereto; and
   each of the fastener members comprising a base and a pair of substantially parallel tissue-piercing prongs extending substantially perpendicularly from the base, the length of the base being substantially equal to the length of the retainer member, each prong being spaced inward from its respective end of the base thereby defining tissue-engaging extensions of the base between each prong and its respective end of the base, said fastener members being oriented in said apparatus in a row parallel to said row of retainer members such that the longitudinal centerlines of said fastener members extend substantially in the direction of the row and the tissue-engaging extensions of each fastener member in the row nearly touch a tissue-engaging extension of each fastener member adjacent thereto, thereby providing essentially total hemostasis when the fasteners are applied to tissue.

9. The combination of claim 8 wherein said pusher means comprises a plurality of pusher members corresponding to said plurality of surgical fasteners, each of said pusher members having a face for pushing against the base of a respective one of said fastener members, the length of the face of each pusher member parallel to the base of each fastener member being substantially equal to the length of the base of each fastener member so that when each pusher member contacts the base of its respective fastener member, the pusher member exerts pressure along substantially the entire length of the base of its respective fastener member.

10. The combination of claim 9 wherein the fastener members and retainer members are made of a resinous material.

11. The combination of claim 10 wherein the resinous material is absorbable in the body.

12. The combination of claim 9 wherein the prongs of the fastener member are substantially equidistant from the transverse centerline of the base of the fastener member.

13. The combination of claim 12 wherein the fastener members and retainer members are made of a resinous material.

14. The combination of claim 13 wherein the resinous material is absorbable in the body.

* * * * *